US011617843B2

(12) United States Patent
Jiang et al.

(10) Patent No.: US 11,617,843 B2
(45) Date of Patent: Apr. 4, 2023

(54) ELASTIC ELECTRODE STRUCTURE FOR ELECTRONIC CIGARETTE

(71) Applicant: Shenzhen First Union Technology Co., Ltd., Shenzhen (CN)

(72) Inventors: Zhanjun Jiang, Shenzhen (CN); Yonghai Li, Shenzhen (CN); Zhongli Xu, Shenzhen (CN)

(73) Assignee: Shenzhen First Union Technology Co., Ltd., Shenzhen (CN)

(*) Notice: Subject to any disclaimer, the term of this patent is extended or adjusted under 35 U.S.C. 154(b) by 1350 days.

(21) Appl. No.: 15/990,060

(22) Filed: May 25, 2018

(65) Prior Publication Data

US 2018/0338534 A1    Nov. 29, 2018

(30) Foreign Application Priority Data

May 25, 2017   (CN) .......................... 201720590989.5

(51) Int. Cl.
| | | |
|---|---|---|
| *A61M 15/06* | (2006.01) | |
| *A61M 11/04* | (2006.01) | |
| *H01M 50/20* | (2021.01) | |
| *H01M 50/24* | (2021.01) | |
| *H01M 50/531* | (2021.01) | |
| *A24F 40/40* | (2020.01) | |
| *A24F 40/10* | (2020.01) | |

(Continued)

(52) U.S. Cl.
CPC ............. *A61M 15/06* (2013.01); *A24F 40/40* (2020.01); *A61M 11/042* (2014.02); *H01M 50/20* (2021.01); *H01M 50/24* (2021.01); *H01M 50/531* (2021.01); *H01M 50/572* (2021.01); *A24F 40/10* (2020.01); *A61M 2205/8206* (2013.01); *H01M 2220/30* (2013.01); *H01R 13/24* (2013.01)

(58) Field of Classification Search
CPC .............................. H01M 50/20; A61M 15/06
See application file for complete search history.

(56) References Cited

U.S. PATENT DOCUMENTS

2014/0150783 A1    6/2014  Liu

FOREIGN PATENT DOCUMENTS

| CN | 101 627 837 A | 1/2010 |
|---|---|---|
| CN | 102 894485 A | 1/2013 |
| CN | 203416812 U * | 2/2014 |

(Continued)

*Primary Examiner* — Maria Laios
*Assistant Examiner* — Jordan E Berresford
(74) *Attorney, Agent, or Firm* — PROI Intellectual Property US; Klaus Michael Schmid

(57) ABSTRACT

An elastic electrode structure for an electronic cigarette is disclosed. The electronic cigarette includes an atomizing assembly and a battery assembly. The battery assembly has a threaded sleeve arranged on an upper end thereof. The elastic electrode structure includes an electrode ring arranged in the threaded sleeve. The electrode ring has a lower end extending out from a through hole defined at the bottom of the threaded sleeve. The elastic electrode structure further includes an insulating ring arranged between the electrode ring and the threaded sleeve, and the elastic electrode structure further includes an elastic sealing ring arranged between the electrode ring and the insulating ring. The elastic electrode structure has good leak-proofing effect and low cost.

7 Claims, 2 Drawing Sheets

(51) Int. Cl.
*H01M 50/572* (2021.01)
*H01R 13/24* (2006.01)

(56) References Cited

FOREIGN PATENT DOCUMENTS

| | | | |
|---|---|---|---|
| CN | 203762297 U | * | 8/2014 |
| EP | 2 801 270 A2 | | 11/2014 |
| WO | 20150106440 A1 | | 7/2015 |

* cited by examiner

ELASTIC ELECTRODE STRUCTURE FOR ELECTRONIC CIGARETTE

TECHNICAL FIELD

The present disclosure relates to the technical field of electronic cigarettes, and particularly, to an elastic electrode structure for an electronic cigarette.

BACKGROUND

Tobacco smoke contains dozens of carcinogens (for example, tar), which are believed to have a great harm to human health. Furthermore, the smoke hangs in air, making the surrounding people passive to breathe and causing damages to their bodies. Therefore, most public places have expressly forbidden smoking. In order to meet the need of some smokers, electronic cigarette appears accordingly.

Current electronic cigarettes include an atomizing assembly and a battery assembly. When in use, some of the tobacco liquid is easy to flow to the inside of the battery assembly from top to bottom. The leaked liquid enters the battery assembly through an electrode and causes short circuit of a main board, thereby seriously impacting user experience. For example, Chinese patent with Publication Number CN201210408618.2 discloses "An atomizing device, an atomizer and an electronic cigarette", as shown in FIG. 9. The electronic cigarette has an atomizing sleeve 9 on an upper end thereof, and a battery 18 on a lower end thereof. When in use, the atomizing sleeve 9 and the battery 18 are connected together through a thread. However, some of the tobacco liquid probably leaks in the battery through a gap between a threaded sleeve and an electrode ring to cause damage to the battery.

SUMMARY

The technical problem to be solved by the present disclosure is to overcome the drawbacks in the prior art and provide an elastic electrode structure for electronic cigarettes that is simple in structure, has low cost and can effectively prevent liquid leakage.

In order to solve the above technical problem, the present disclosure employs a technical scheme as follows. An elastic electrode structure for an electronic cigarette is provided. The electronic cigarette includes an atomizing assembly and a battery assembly. The battery assembly has a threaded sleeve arranged on an upper end thereof. The elastic electrode structure includes an electrode ring arranged in the threaded sleeve. The electrode ring has a lower end extending out from a through hole defined at the bottom of the threaded sleeve. The elastic electrode structure further includes an insulating ring arranged between the electrode ring and the threaded sleeve, and the elastic electrode structure further includes an elastic sealing ring arranged between the electrode ring and the insulating ring.

The insulating ring has a flange on an upper end thereof, and the flange has an outer diameter greater than an inner diameter of the through hole.

The electrode ring has an end part, and the end part has a diameter greater than an inner diameter of a hollow ring-shaped part of the insulating ring.

A spring is arranged between the periphery of the electrode ring and an inner side of the insulating ring, and the spring is located in the hollow ring-shaped part.

The sealing ring has an upper end abutting against the underside of the end part of the electrode ring, and the sealing ring has a lower end abutting against the flange on the upper end of the insulating ring.

The sealing ring is a hollow body, and the sealing ring has openings on both upper and lower ends thereof; and the electrode ring passes through both the openings on the upper and lower ends of the sealing ring.

The sealing ring has a diamond part on a middle part thereof; in a natural state, the diamond part and an inner wall of the threaded sleeve have a gap therebetween; and, in a working state, the diamond part abuts against the inner wall of the threaded sleeve.

Insulating silica gel is arranged on the periphery of a lower end of the threaded sleeve.

An electrode cap is connected to a bottom end of the sealing ring.

The sealing ring is made of silica gel.

The present disclosure has the following beneficial effects: the sealing ring made of silica gel is arranged between the electrode and the insulating ring, thereby achieving a very good sealing effect for the gap between the electrode and the insulating ring; in a working state, the sealing ring is squeezed to deform, thereby achieving a better sealing effect. The sealing ring can also make the electrode ring stressed evenly, so that the electrode ring will not tilt at an angle in working state.

DETAILED DESCRIPTION

The elastic electrode structure for an electronic cigarette according to the present disclosure is described below in further detail in conjunction with the drawings.

Figure 1:
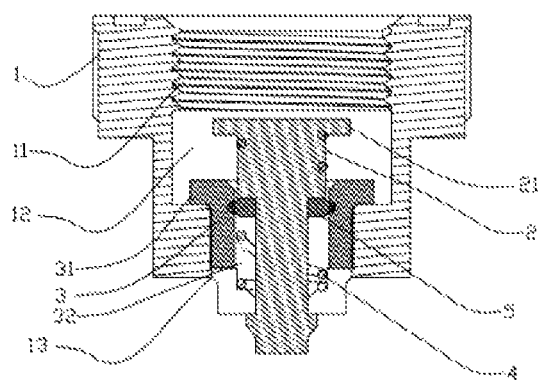
FIG. 1 is a cross-sectional view of a first embodiment of an elastic electrode structure for an electronic cigarette according to the present disclosure.
Figure 2:
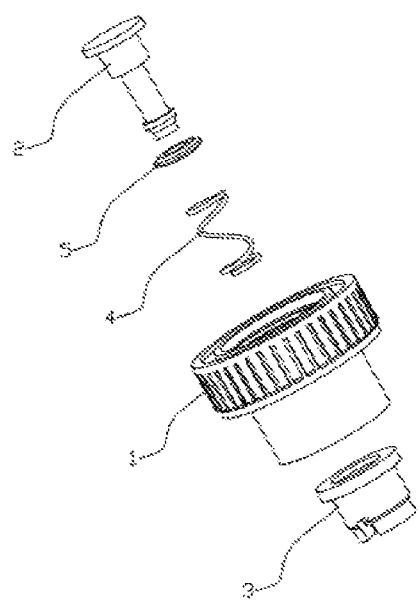
FIG. 2 is an exploded view of a first embodiment of an elastic electrode structure for an electronic cigarette according to the present disclosure.

Reference is made to FIG. 1 and FIG. 2, which show a first embodiment of the elastic electrode structure for an electronic cigarette. The electronic cigarette includes an atomizing assembly. The atomizing assembly has a lower end connected to a battery assembly. As shown in FIG. 1, the battery assembly has a threaded sleeve 1 arranged on an upper end thereof. The atomizing assembly is not shown in FIG. 1 and FIG. 2. The atomizing assembly has a lower end connected to the upper end of the battery assembly through thread. The threaded sleeve 1 has an internal thread 11, that is to say, the atomizing assembly and the battery assembly are in threaded connection through the threaded sleeve 1. The threaded sleeve 1 has an inner chamber 12. The inner chamber 12 is located below the internal thread 11. The inner chamber 12 has an electrode ring 2 arranged therein. The electrode ring 2 has an upper end located in the inner chamber 12, and the electrode ring 2 has a lower end extending out through a through hole 13 defined at the bottom of the threaded sleeve 1.

The elastic electrode structure includes an insulating ring 3 arranged between the electrode ring 2 and the threaded sleeve 1. The insulating ring 3 is sleeved on the periphery of the electrode ring 2. The insulating ring 3 has a flange 31 on an upper end thereof, and the flange 31 has an outer diameter greater than an inner diameter of the through hole 13. The insulating ring 3 has a hollow ring-shaped part 32. The electrode ring 2 has an end part 21. The end part 21 has a diameter greater than an inner diameter of the hollow ring-shaped part 32. Therefore, the end part 21 achieves a limit function. A spring 4 is arranged between the periphery of the electrode ring 2 and an inner side of the insulating ring 3. The spring 4 is located in the hollow ring-shaped part 32. The elastic electrode structure further includes an elastic sealing ring 5 arranged between the electrode ring 2 and the inner side of the insulating ring 3. The elastic sealing ring 5 is sleeved on the periphery of the electrode ring 2, and the sealing ring 5 is in tight contact with the inner side of the insulating ring 3. The sealing ring 5 desirably is made of silica gel. In this way, when the electrode ring 2 is pressed downwards, even though the sealing ring 5 is deformed, the sealing ring 5 can still well seal the gap between the electrode ring 2 and the insulating ring 3. Therefore, it is guaranteed that no tobacco liquid leaks downwards from there.

Figure 3:
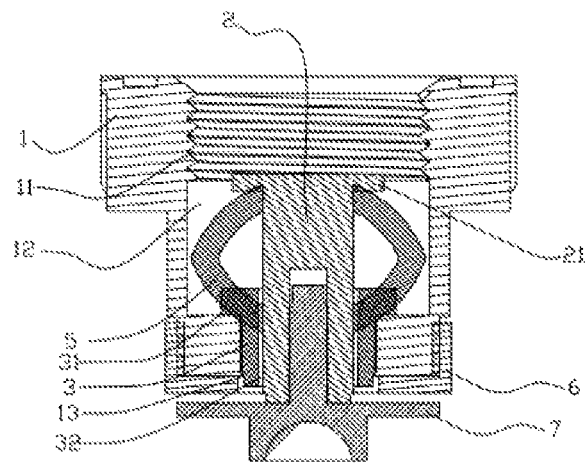
FIG. 3 is a cross-sectional view of a second embodiment of an elastic electrode structure for an electronic cigarette according to the present disclosure.
Figure 4:
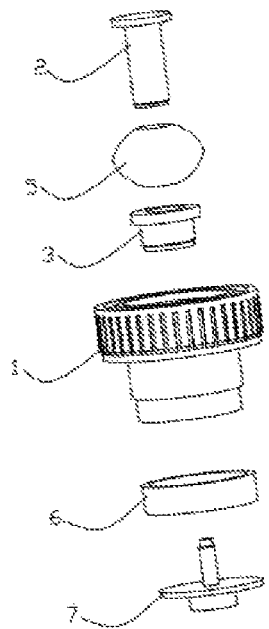
FIG. 4 is an exploded view of a second embodiment of an elastic electrode structure for an electronic cigarette according to the present disclosure.

Reference is made to FIG. 3 and FIG. 4, which show a second embodiment of the elastic electrode structure for an electronic cigarette. The electronic cigarette includes an atomizing assembly. The atomizing assembly has a lower end connected to a battery assembly. As shown in FIG. 3, the battery assembly has a threaded sleeve 1 arranged on an upper end thereof. The atomizing assembly is not shown in FIG. 3 and FIG. 4. The atomizing assembly has a lower end connected to the upper end of the battery assembly through thread. The threaded sleeve 1 has an internal thread 11, that is to say, the atomizing assembly and the battery assembly are in threaded connection through the threaded sleeve 1. The threaded sleeve 1 has an inner chamber 12. The inner chamber 12 is located below the internal thread 11. The inner chamber 12 has an electrode ring 2 arranged therein. The electrode ring 2 has an upper end located in the inner chamber 12, and the electrode ring 2 has a lower end extending out through a through hole 13 defined at the bottom of the threaded sleeve 1.

The elastic electrode structure includes an insulating ring 3 arranged between the electrode ring 2 and the threaded sleeve 1. The insulating ring 3 is sleeved on the periphery of the electrode ring 2. The insulating ring 3 has a flange 31 on an upper end thereof, and the flange 31 has an outer diameter greater than an inner diameter of the through hole 13. The insulating ring 3 has a hollow ring-shaped part 32. The electrode ring 2 has an end part 21. The end part 21 has a diameter greater than an inner diameter of the hollow ring-shaped part 32. Therefore, the end part 21 achieves a limit function. The elastic electrode structure further includes an elastic sealing ring 5 arranged between the electrode ring 2 and the insulating ring 3. The elastic sealing ring 5 is sleeved on the periphery of the electrode ring 2. The elastic sealing ring 5 has an upper end abutting against the underside of the end part 21 of the electrode ring 2, and the sealing ring 5 has a lower end abutting against the flange 31 on the upper end of the insulating ring 3. The sealing ring 5 and the insulating ring 3 are in tight contact. The sealing ring 5 can be a hollow spherical body, a hollow elliptical body, etc. The sealing ring 5 has openings on both upper and lower ends thereof. The electrode ring 2 passes through both the openings on the upper and lower ends of the sealing ring 5. The sealing ring 5 desirably is made of silica gel. In this way, when the electrode ring 2 is pressed downwards, even though the sealing ring 5 is deformed, the sealing ring 5 can still well seal the gap between the electrode ring 2 and the insulating ring 3. Therefore, it is guaranteed that no tobacco liquid leaks downwards from there. In addition, there is a little gap between an edge diamond part of the sealing ring 5 and an inner wall of the threaded sleeve 1. When the electrode ring 2 is pressed downwards, the sealing ring 5 is deformed, and the diamond part becomes larger until the diamond part is in tight contact with the inner wall of the threaded sleeve 1. Therefore, a further sealing effect can be achieved. Insulating silica gel 6 is arranged on the periphery of a lower end of the threaded sleeve 1. An electrode cap 7 is connected to a bottom end of the sealing ring 5.

In the first embodiment and the second embodiment, the sealing ring 5 not only achieves a sealing function, but also makes the electrode ring 2 stressed evenly, so that the electrode ring 3 will not tilt at an angle in working state, and good contact is kept between the battery assembly and the lower end of the atomizing assembly, that is, the stable power supply to the atomizing assembly is guaranteed.

The above embodiments are merely partial implementations listed in the description to help understand the content of the present disclosure, and they neither restrict the technical scheme of the present disclosure, nor make an exhaustion of all schemes implementable. Any minor improvements or equivalent substitutions made to the structures, processes or steps of the present disclosure are intended to be included in the scope of protection of the present disclosure.

What is claimed is:

1. An elastic electrode structure for an electronic cigarette, the electronic cigarette comprising an atomizing assembly and a battery assembly, the battery assembly having a threaded sleeve arranged on an upper end thereof, and the elastic electrode structure further comprising an electrode ring arranged in the threaded sleeve, wherein the electrode ring has a lower end extending out from a through hole defined at the bottom of the threaded sleeve, the elastic electrode structure further comprises an insulating ring arranged between the electrode ring and the threaded sleeve, and the elastic electrode structure further comprises an elastic sealing ring arranged between the electrode ring and the insulating ring;
   wherein the insulating ring has a flange on an upper end thereof, and the flange has an outer diameter greater than an inner diameter of the through hole;
   wherein the electrode ring has an end part, and the end part has a diameter greater than an inner diameter of a hollow ring-shaped part of the insulating ring;
   wherein the sealing ring has an upper end abutting against underside of the end part of the electrode ring, and the sealing ring has a lower end abutting against the flange on the upper end of the insulating ring.

2. The elastic electrode structure according to claim 1, wherein a spring is arranged between a periphery of the electrode ring and an inner side of the insulating ring, and the spring is located in the hollow ring-shaped part.

3. The elastic electrode structure according to claim 1, wherein the sealing ring is a hollow body, and the sealing ring has openings on both upper and lower ends thereof; and the electrode ring passes through both the openings on the upper and lower ends of the sealing ring.

4. The elastic electrode structure according to claim 3, wherein the sealing ring has a diamond part on a middle part thereof; in a natural state, the diamond part and an inner wall of the threaded sleeve have a gap therebetween; and, in a working state, the diamond part abuts against the inner wall of the threaded sleeve.

5. The elastic electrode structure according to claim 1, wherein insulating silica gel is arranged on the periphery of a lower end of the threaded sleeve.

6. The elastic electrode structure according to claim 1, further comprising an electrode cap, wherein the electrode cap is connected to a bottom end of the sealing ring.

7. The elastic electrode structure according to claim 1, wherein the sealing ring is made of silica gel.

* * * * *